(12) United States Patent
Mound

(10) Patent No.: US 7,310,581 B2
(45) Date of Patent: Dec. 18, 2007

(54) BULK MATERIAL ANALYZER SYSTEM

(75) Inventor: Michael Mound, Baden (CH)

(73) Assignee: ABB Schweiz AG (CH)

( * ) Notice: Subject to any disclaimer, the term of this patent is extended or adjusted under 35 U.S.C. 154(b) by 0 days.

(21) Appl. No.: 11/474,477

(22) Filed: Jun. 26, 2006

(65) Prior Publication Data

US 2007/0265783 A1  Nov. 15, 2007

(30) Foreign Application Priority Data

May 10, 2006  (EP) .................... 06405196

(51) Int. Cl.
*G06F 19/00* (2006.01)
(52) U.S. Cl. .............. 702/28; 702/123; 702/124; 702/126; 702/182; 702/189; 356/326; 356/328; 250/339.05
(58) Field of Classification Search ............. 702/28, 702/180–186, 106, 122–126, 30–34, 189; 356/326, 328, 31, 38; 250/360.1, 339.05
See application file for complete search history.

(56) References Cited

U.S. PATENT DOCUMENTS

| | | | |
|---|---|---|---|
| 4,508,573 A | 4/1985 | Harris | 106/100 |
| 4,799,880 A | 1/1989 | McCoy | 432/13 |
| 4,976,540 A | 12/1990 | Kitamura et al. | 356/38 |
| 5,754,423 A | 5/1998 | Teutenberg et al. | 364/148 |
| 6,160,618 A | 12/2000 | Garner | 356/318 |
| 6,491,751 B1 | 12/2002 | Watson | 106/756 |
| 6,709,510 B1 | 3/2004 | Young et al. | 106/745 |
| 6,771,369 B2 | 8/2004 | Rzasa et al. | 356/326 |
| 2003/0123056 A1* | 7/2003 | Barnes et al. | 356/300 |
| 2004/0031335 A1* | 2/2004 | Fromme et al. | 73/865 |
| 2004/0207842 A1 | 10/2004 | Rzasa et al. | 356/328 |
| 2004/0232339 A1* | 11/2004 | Lanoue | 250/339.05 |
| 2005/0077471 A1 | 4/2005 | Edwards et al. | 250/360.1 |

FOREIGN PATENT DOCUMENTS

| | | |
|---|---|---|
| WO | WO 02/065072 | 8/2002 |
| WO | WO 02/065100 | 8/2002 |
| WO | WO 02/065101 | 8/2002 |
| WO | WO 02/065102 | 8/2002 |
| WO | WO 2002/088811 | 11/2002 |
| WO | WO 2004/106874 | 12/2004 |
| WO | WO 2004106874 A1 * | 12/2004 |

(Continued)

OTHER PUBLICATIONS

European Search Report; Oct. 6, 2006; 7 Pages.

(Continued)

*Primary Examiner*—Phuong Huynh
(74) *Attorney, Agent, or Firm*—St. Onge Steward Johnston & Reens LLC

(57) ABSTRACT

A real-time bulk material analyzing system is disclosed for analyzing the elemental characteristics of bulk material passing by the system on a moving conveyor belt. An exemplary embodiment includes a source of illumination emitting white light for exciting bulk material to be analyzed, and a hyperspectral imaging spectrometer for capturing spectral reflectance from bulk material excited by the illumination source. A non-hazardous source of excitation can be used, which allows the bulk material to pass unobstructed and undisturbed through the detector array.

12 Claims, 2 Drawing Sheets

FOREIGN PATENT DOCUMENTS

| | | | |
|---|---|---|---|
| WO | WO 2006/054154 | | 5/2006 |
| WO | WO 2006054154 A1 | * | 5/2006 |

OTHER PUBLICATIONS

Advanced Spaceborne Thermal Emission and Reflection Radiometer; ASTER (Japanese Ministry of Economy, Trade and Industry and NASA); www.asterweb.jpl.nasa.gov; 83 pages.

Analytical Spectral Devices, Inc.; Field Spectrometry: Techniques and Instrumentation; Boulder, Colorado; 2001; 9 pages.

Analytical Spectral Devices, Inc.; Identification of raw materials by NIR reflectance; Boulder, Colorado; www.asdi.com; 8 pages.

Analytical Spectral Devices, Inc.; Introduction to NIR Technology; Boulder, CO; www.asdi.com; 10 pages.

Analytical Spectral Devices, Inc.; NIR Analysis of White Powder Samples; Boulder, Colorado; www.asdi.com; 4 pages.

Analytical Spectral Devices, Inc; Quantitative Analysis of Concrete Samples Via NIR; Bolder, Colorado; www.asdi.com; 2004; 7 pages.

Clark, R. N.; Spectroscopy of Rocks and Minerals, and Principles of Spectroscopy, in *Manual of Remote Sensing*, Chapter 1: vol. 3, *Remote Sensing for the Earth Sciences*, (A.N. Rencz, ed.) John Wiley and Sons, New York, p. 3-58, 1999; 67 pages.

CTR Carinthian Tech Research AG; Spectral Imaging Brochure; www.ctr.at; 2 pages.

Leetham, Darrell, et al.; Flexibility in Online Analysis; USA; www.thermo.com; 6 pages.

Perkinson, Maire-Claire et al.; Low Cost Hyperspectral Imaging From Space; England; 4 pages.

Stevens, Dave et al.; Recent Developments in Hyperspectral Imaging and their Significance as a New and Important Direct Exploration Tool; 26 pages.

* cited by examiner

BULK MATERIAL ANALYZER SYSTEM

RELATED APPLICATIONS

The present application claims priority under 35 U.S.C. §119 to European Application No. 06405196.4 filed May 10, 2006, the contents of which are hereby incorporated by reference in their entirety.

BACKGROUND

A real-time bulk material analyzing system is disclosed for analyzing the elemental characteristics of bulk material being transported on a conveyor belt.

Conveyor belts are extensively used to transport bulk materials such as Limestone, Bauxite, Copper ore, Zinc ore, Lead ore, Iron ore, Silica, Phosphate rock, Potash, Clay, Rare earths, Scrap materials, Chalk, Coal and coke, Alumina, Marl, Pyrite, Fly ash, etc. A conveyor belt includes two end pulleys, with a continuous belt that rotates about them in a continuous unending loop. The pulleys are powered, moving the belt and the loaded bulk material on the belt forward at fixed or variable speeds. Certain industrial applications require analyzing the exact or averaged composition of the bulk material which is transported on conveyor belts from one process point to another.

Bulk Materials are normally characterized in their raw material (pre-blended) states or following a blending (physical mixture of component raw materials) procedure via a system of proportioning feeders from bins or silos containing relatively homogeneous compositional characteristics.

Analysis of either raw material components or blended materials has been accomplished by extracting samples and transporting them either manually or via an automatic "tube post" pneumatic sampling and conveying system to a central laboratory for analysis where they are subject to analysis. The results are then communicated to a variety of means for adjusting proportions to meet e.g. a desired blend recipe.

This arrangement, while providing high accuracies, cannot meet the needs of real-time analyses for rapid and real-time control, as the time required for sampling, splitting, transport, preparation, and analysis can vary from a minimum of several minutes to an hour or more. During this delay, the fast-moving materials represented by the sample analyzed have long passed points of control and adjustments which are then made in response to results from the analysis of the samples might be inadequate or simply too late for corrective actions taken.

A basic solution sought by the bulk material processing industry is to analyze the materials as they pass through, or are exposed in some manner, to analytical systems while the materials remain both physically and chemically unchanged and pass uninterruptedly on their bed located on the moving conveyor belt. No attempt to stop or otherwise slow the speed of the conveyor belt merely to accommodate analysis is normally desired nor permitted as a necessary restriction on allowing production and processing in such production environments.

A few methods to achieve elemental, and thereby, oxide forms of the chemical constituents of the various raw or blended materials have been put into current practice. They are however limited in numbers in terms of practical application and are mainly making use of neutron activation systems. These so-called Prompt Gamma Neutron Activation Analysis (PGNAA) systems require either radioactive isotopes for neutron flux, such as the isotope of Californium, $Cf_{252}$, or a neutron generator (tube). Neutron activation systems apply a potentially hazardous to humans technique which requires protective permanent careful shielding to humans via direct or indirect exposure and costly isotope or generator tube replacements. The short half-life of $Cf_{252}$ at only approximately two and a half years and the requirement for replacement of neutron tube generators, normally every one to one and a half years, represent both expensive maintenance costs as well as difficulties in convincing authorities of the safety in transport and operation of both these neutron sources. Further, the resultant gamma radiation from the analyzed bulk materials, which is caused by neutron activation of the nuclei of the irradiated materials, represents additional health and environmental hazards.

Other techniques that have been attempted, such as high-power X-ray systems, or X-ray diffraction systems, also involve strict adherence to local regulatory authorities. In some venues, the presence of such devices is prohibited altogether.

US 2003/0123056 discloses a hyperspectral imaging instruments array for exploiting detailed multispectral, hyperspectral and ultraspectral imaging and non-imaging signature information. This is accomplished in real-time in order to identify the unique spectral characteristics of the target. The instruments array contains at least one mechanically integrated hyperspectral sensor installed on a fixed or moveable hardware frame and co-boresighted with a similarly mounted digital camera, calibrated visible light source, calibrated thermal source and calibrated fluorescence source on a small spot on the target. The target is moved across the array, allowing the array to effect collection of absolute radiometrically corrected spectral data against the target at high spatial and spectral resolutions.

As hyperspectral imaging spectrometers cannot penetrate to depth hyperspectral imaging has not been considered a practical means for real-time elemental bulk material analysis.

SUMMARY

A real-time bulk material analyzing system is disclosed for analyzing the elemental characteristic of varying bulk material passing unobstructed and undisturbed under or through a detector array, said analyzing system comprising a non-hazardous source of excitation.

An exemplary real-time bulk material analyzing system comprises a consistent white light emitting source of illumination for exciting the bulk material and a hyperspectral imaging spectrometer for capturing spectral reflectance from the bulk material exposed to the white light.

The use of hyperspectral techniques allows for characterization via various versions of reflectance or absorption by white light, such as, but not limited to NIR of varying wave lengths, laser techniques (LIBS=Laser Induced Breakdown Spectroscopy) by use of
 (a) a source of light,
 (b) an array of beam splitting and collecting spectral components using collimating gratings, thermal detectors, or plasma generators, and
 (c) an array of detectors within small, robust spectrometers to provide a spectral signature.

The bulk material can be excited by being illuminated by light directed onto the bulk material from a light source that can be set to different frequencies so as to further enhance imaging of the bulk material by causing the bulk material to reflect or absorb the light at characteristic and identifiable wavelengths.

In stockpile building, the output of the secondary crusher can be approximately homogeneous. Therefore, with an exemplary real-time bulk material analyzing system, bulk material can be analyzed without exposing the material or the environment to hazardous radiation as would be the case with deep or fully penetrating systems.

Some of the main benefits of exemplary embodiments of a real-time bulk material analyzing system as disclosed herein are represented by

- a much lower cost of acquisition (an end-user price is expected to be approximately 25% that of conventional neutron, i.e., PGNAA, on-line analyzers),
- its relatively low maintenance and ease of use and control as no technical expertise is required to put into operation or use on a regular basis,
- its lower total cost of ownership thanks to it's simplicity, robustness and ease of use,
- its versatility owing to the natural consequence of the identification of a large number of different elements can be measured simultaneously both qualitatively and quantitatively,
- its non-hazardous nature as no X-ray or neutron activation systems sources are used to excite the material to be analyzed,
- its robustness (suited for harsh production plant environments). This is because, for example, hyperspectral imaging devices have been housed and packaged to withstand the rigors of space environments, extremes of temperatures and all varieties of climates in unprotected terrestrial, aerial, and space-related venues, and
- its portability as no extensive shielding is required due to the absence of any hazardous excitation source.

BRIEF DESCRIPTION OF THE DRAWINGS

Some of the features, advantages, and benefits of the present invention having been stated, others will become apparent as the description proceeds when taken in conjunction with the accompanying drawings in which.

DETAILED DESCRIPTION

Exemplary embodiments will now be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
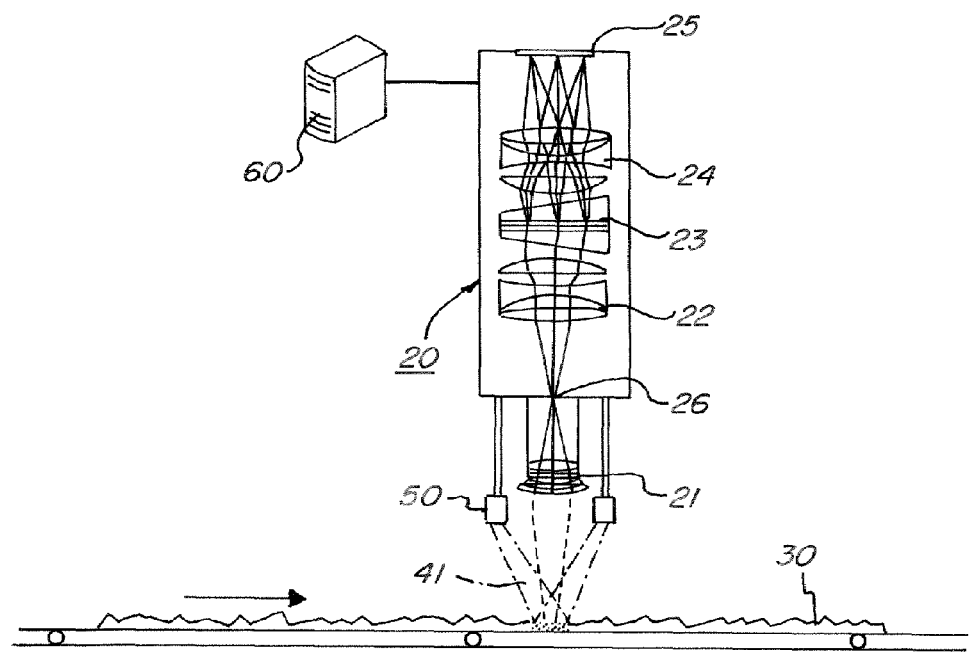
FIG. 1 schematically shows a side-view of an exemplary bulk material analyzing system.

As shown in FIG. 1, an exemplary bulk material analyzing system comprises a hyperspectral imaging spectrometer 20 which is installed above a moving conveyor belt 10 which will carry the bulk material 30 to be analyzed. An illumination source emitting white light is installed somewhere in the vicinity of the sensor, preferably aiming a thin but wide beam of light on the bulk material across the conveyor belt. The illumination source may comprise several light emitters arranged above the conveyor belt.

Figure 3:
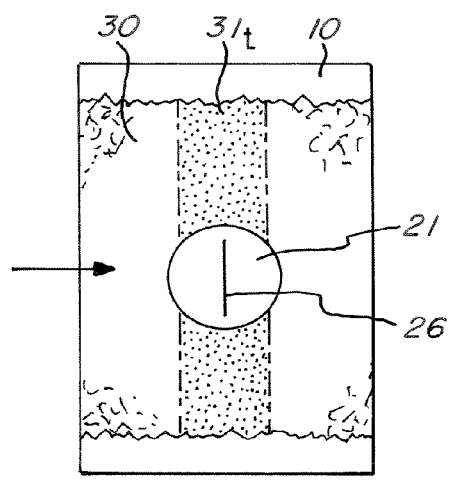
FIG. 3 shows an enhanced close-up of the top-view of the bulk material analyzing system of FIG. 2 schematically showing the entrance slit of the hyperspectral imaging spectrometer.

The hyperspectral imaging spectrometer comprises several optical components. The front lens 21 is installed at a predefined height above the conveyor belt. It focuses on a small stripe on the conveyor belt which is illuminated by the light emitted by the illumination source 50. A small entrance slit 26 which is arranged on a plate behind the front lens acts as a field-stop to determine the field of view in spatial direction across the conveyor belt which will be scanned by the hyperspectral imaging spectrometer. FIG. 3 shows a close-up of the entrance slit 26 and schematically shows the covered area $31_t$ of the bulk material 30. Behind the entrance slit and a collimating lens 22, the optical components used for separating the directions of propagation of radiations of different wavelengths are arranged. In the exemplary embodiment this is done by a prism-grating-prism component, after which a focusing lens 24 aligns the beams of different wavelengths so that they can be captured by a two dimensional CCD array 25. A CCD (charge-coupled device) array is an sensor for recording images, consisting of an integrated circuit containing an array of linked, or coupled, capacitors. The output signal 42 of a CCD-array can be processed in a control unit 60 which is connected to the hyperspectral imaging spectrometer 20. The control unit 60 can comprise a computer having at least one processor and memory. The output signals of the CCD-array can be transmitted via a fiber optic or a high bandwidth cable or radio frequency link.

Figure 2:
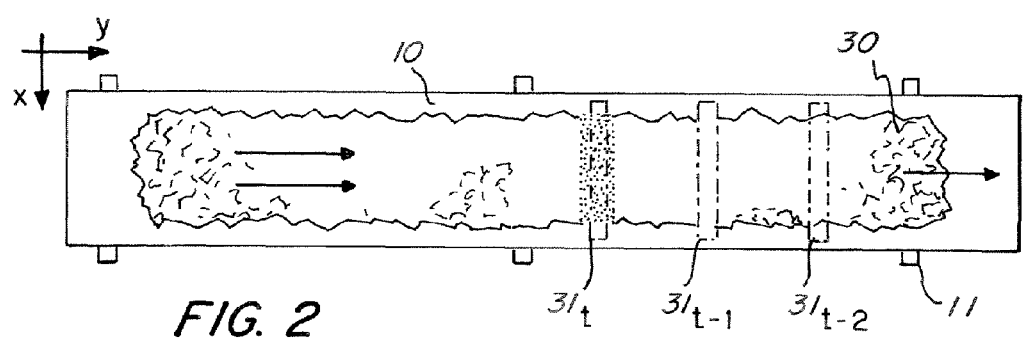
FIG. 2 schematically shows a top-view of the bulk material analyzing system of FIG. 1.

FIG. 2 shows a top-view of the conveyor belt 10 moving left to right and carrying bulk material 30. Marked with doted rectangles are the scanned areas on the conveyor belt. As the bulk material passes by the hyperspectral imaging spectrometer, snapshot scans are taken either continuously, in regular periods or on demand.

For each scan, e.g. the most recent scan of area $31_t$, a two dimensional output array is generated by the hyperspectral imaging spectrometer and forwarded to the control unit for further processing.

Figure 4:
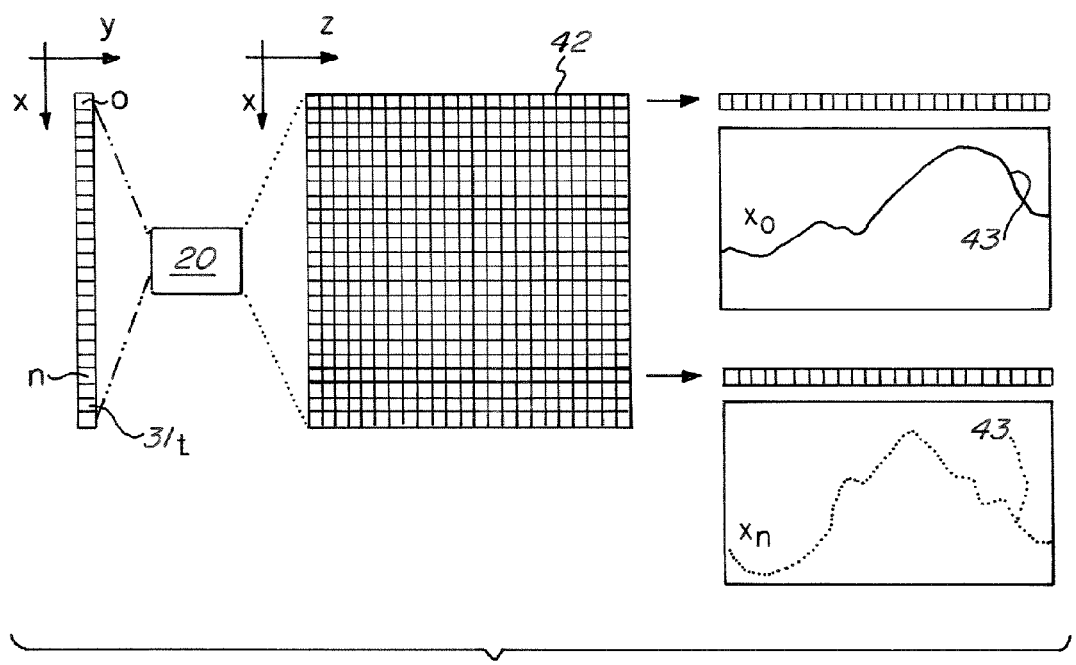
FIG. 4 schematically shows the conversion of the one-dimensional spherical scan to the two-dimensional spherical/spectral image and to the spectral signature.

As shown in FIG. 4, the two dimensional output array comprises values representing the amount of energy of a certain wavelength reflected from the bulk materiel across the conveyor belt. One dimension of the array corresponds to the spherical distribution across the conveyor belt (x-axis) and on the other dimension corresponds to the range of wavelength of the reflected energy (z-axis). Each captured spot of bulk material across the conveyor belt has its own spectral signature 43 representing the energy reflected by the bulk material in that particular spot distributed according to the wavelength.

To factor the spherical distribution along the conveyor belt (y-axis) into the output signals the two dimensional output array of several timely separated scans can be stacked defining a three dimensional cube.

To facilitate the spectral analysis the resolution of the two-dimensional output array can be reduced across the x-axis. In one such particularly simple embodiment of the bulk material analyzing system, the resolution of the output array across the x-axis is reduced to one pixel so that for the entire width of the conveyor belt there is only one spectral signature forwarded to the control unit. This single spectral signature is then analyzed and compared to a set of previously recorded and stored spectral signatures of possible material composition. In most conveyor belt applications, the distribution of different materials across the conveyor belt is not of importance as only the composition of the bulk material, i.e. the existence of specific ingredients in the right quantity, matters. This application with a reduced resolution of the spectrometer can be used in applications with only a small number of possible ingredients to be observed.

In an exemplary bulk material analyzing system, only white light is required for constant illumination to provide for a source of illumination for infra-red splitting to cause reflective spectral structure of contained bulk materials. Infra-red, including NIR (near infra-red), VNIR (Visual near infra-red), SWIR (Short-Wave Infra-red), and TIR (Thermal Infra-red), spans a wavelength range of 250 to 2500 nanometers (nm) for the purposes of elemental characterization of materials.

As bulk material often comprises oxidized material, oxides can be recognized in accordance with exemplary embodiments, and converted to elemental form. Oxides can be reported via built-in calculations of standard conversions from elements to their oxide forms. As an example: aluminum, Al, can be converted to aluminum-oxide, $Al_2O_3$ by an automatic conversion factor of 1.8895 times the reported quantity of the element Al. Similar conversion factors are readily made for reporting purposes for any detected element of interest. These conversion factors are standard for reporting results based on known chemical properties of all elements in their atomic or molecular forms and can be provided as reported results of analyses using simple calculations built into the device software.

Several such spectrometers may be used to effectively provide for the strongest signal to noise ratio for several spectral ranges within the wavelengths of the elements to be analyzed. In an arrangement of several spectrometers, each of the spectral sensors can be co-boresighted so that an imaginary straight line extends from the center of each sensor to a common point on the bulk material to be analyzed. Alternatively, in an arrangement of several spectrometers overlapping spectral reports can be made by precise angling of the spectrometers used to provide a scanned strip-step across the width of the conveyor belt.

The process of analyzing bulk material with the exemplary bulk material analyzing system comprises the following steps:

In a first step, a two dimensional spherical/spectral picture is captured by the CCD array. The radiation from the entrance slit 26 is collimated by a lens 22 and then dispersed by a dispersing element 23, in the exemplary embodiment a prism-grating-prism element, so that the direction of propagation of the radiation depends on its wavelength. It is then focused by a focusing lens 24 on an image plane, where the image is captured by the two-dimensional detector, the CCD Array 25. The CCD Array produces an output signal of reflected energy at specific wavelength 42. Every point along the spherical axis (see FIG. 4, points 0 and n on the x-axis across the conveyor belt) is represented on the two dimensional image plane by a series of monochromatic images forming a continuous spectrum in the direction of the spectral axis, which is later converted into the spectral signature 43.

The spectral signatures are created from the two dimensional spherical/spectral picture captured by the CCD Array. Each spot across the spherical x-axis on the conveyor belt has its own one-dimensional spectral signature.

In a second step, the spectral signature of each spot is compared to a set of stored calibrations representing expected concentrations of previously characterized standards. This is done in real time with the help of computer software. As a result, the materialistic characteristic of each spot on the bulk material distributed across the conveyor belt is identified.

In a next step, the information of all single spots is gathered to get the overall distribution of material within the scanned bulk material. Specific elements or their oxides can thereby be identified as to presence and characterized as to concentrations via intensities of detected and recognized spectral signatures.

Any number of chemometric techniques may be used to provide for fitting spectra thus obtained to the stored library of spectra. In the initial calibration of the device, spectra are stored of expected bulk materials to cover all possible ranges of concentrations and mixtures (blends) of elemental contributors to the recovered and resolved spectra. Such acquired spectra are "compared" to the stored spectra to define how the acquired spectra compare to a predicted oxide array. The accuracy of the fit of the acquired spectra and its height difference relative to the standard spectral library stored in the device determines both content and quantity of the elements/oxides based on spectral peaks.

The spectrometers and their contained gratings, beam splitters, detectors, and optical fiber connections, as well as light sources are preferably packaged in a scanning housing fixed at a predetermined height above the moving conveyor belt. The housing thus described is arranged so as to be located normal to the forward directional movement of the belt and its material load.

Applications of this technique are suitable for, but not limited to materials transported by industrial conveyors such as:

Limestone, Shale, Bauxite, Iron ore, Copper ore, Zinc ore, Lead ore, Metalliferous (ferrous and non-ferrous) ores, Silica, Phosphate rock, Potash, Clay, Bentonite, Pharmaceuticals, Manganese, Rare earths, Scrap materials, Chalk, Coal and coke, Alumina, Marl, Pyrite, Fly ash, Slurries of any of the above, Fertilizers containing phosphates, ammoniacal components, potassium/potash, Industrial minerals (ceramics, glass-making raw materials, refractories), Magnesium compounds, Cobalt, Nickel, Titanium, Chrome, Tungsten.

In an exemplary application the bulk material analyzing system can be used in the process of blending of bulk materials used in the manufacture of cement:

Bulk materials are fed to a series of conveyor belts from feeders containing more or less homogeneous crushed rock matter. These materials are generally referred to as cementitious and fusion minerals, which, are to be physically mixed (blended) in a specific proportion prior to being calcined (reduced, in chemical terms) via heating, and then transported, according to the type of cement to be created from said materials.

The proportion of each of the contributing material sources is to be monitored by the inventive bulk material analyzing system so as to correct for more or less richer or poorer grades of components (according to the contained mineral chemistry) by additions of each material as demanded by a control algorithm that obtains real-time chemistry of the bulk materials independently and collectively from results reported by the inventive bulk material analyzing system.

There are four or more key components, which are (in terms of oxides):

| | |
|---|---|
| CaO | normally from high-grade limestone |
| SiO2, | from sand, sandstone in various silicate forms |
| Al2O3 | normally from bauxite or materials high in alumina |
| Fe2O3 | from mill scale, iron ore, or pyrites |

Typical ranges encountered for materials are:

| Dry Basis Oxide | Composition Range (typical value) |
|---|---|
| CaO | 25 . . . 30 . . . 55% |
| SiO2 | 5 . . . 20 . . . 25% |
| Al2O3 | 0 . . . 8% |
| Fe2O3 | 0 . . . 8% |
| MgO | 0 . . . 6% |
| K2O | 0 . . . 3% |
| Na2O | 0 . . . 3% |
| SO3 | 0 . . . 3% |

Accuracies expected for dynamic performance with exemplary embodiments are

| Dry Basis Oxide | Accuracy (RMSD, 1 hour) (%) |
|---|---|
| SiO2 | 0.33 |
| Al2O3 | 0.30 |
| Fe2O3 | 0.08 |
| CaO | 0.32 |
| MgO | 0.29 |
| K2O | 0.21 |
| Na2O | 0.11 |
| SO3 | 0.20 |

Converting from oxide to element from an elemental analysis is obtained, for reporting purposes):

| Dry Basis Oxide | Conversion factor (elemental) |
|---|---|
| SiO2 | 2.1393 |
| Al2O3 | 1.8895 |
| Fe2O3 | 1.4297 |
| CaO | 2.4973 |
| MgO | 1.6581 |
| K2O | 1.2046 |
| Na2O | 1.3480 |

Therefore, the calibration range needs to be broadened to cover low- as well as high-grade limestone, because the presence of MgCO3 in impure limestones is important when blending with higher grades, as too much MgO (exceeding 2.5%, for example) is a genuine quality problem. Usually 5 calibration standards are sufficient.

Alternatively, dilutions may be used to prepare a calibration. This can be accomplished by using a neutral diluent matrix, such as pure limestone of known concentrations of CaO, for example, to make the factoring simple.

In practice, the moisture content, which is what would be expected on conveyor belts, could exceed 5-8% (liter weight %). This is normalized in practice by using a moisture meter (usually a phase-shift microwave device) associated with the monitoring analyzer. Where ambient moisture, including precipitation, is taken into account in atmospherically exposed belt loads, this is a requirement. If moisture can be guaranteed to not exceed 4-5%, then a moisture meter is not necessary, and a mathematical calculation can be made for LOI.

Since the materials will vary in densities, either volumetric or gravimetric measures may be used. If the samples thus prepared are insulated from degradation or deterioration (enclosed in sealed plastic, or similar), they should remain more or less immutable.

A range of calibration samples should, in exemplary embodiments, encompass the typical ranges shown to avoid compromising the analyzer's ability to fit variations into the resultant calibration curve when alternative and (normally) widely varying materials are incorporated into the mix, as one would expect in a typical plant environment. With increasing use of alternative raw materials, the need for analysis increases. If one could expect a narrow bandwidth in concentrations of these key oxides, the need for monitoring would be slight, whereas an analyzer calibrated to capture variations in a broad range (within reasonable limits, of course) becomes more attractive.

The exemplary real-time bulk material analyzing system can be applied to bulk materials in a state of solid particles, powders and slurries.

In the drawings and specification, there have been disclosed exemplary embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

| List of used Abbreviations and Reference Symbols | |
|---|---|
| 10 | Conveyor Belt |
| 11 | Conveyor belt pulleys |
| 20 | Hyperspectral imaging spectrometer |
| 21 | Front Lens with |
| 22 | Collimating lens |
| 23 | Dispersing element, Prism-grating-prism |
| 24 | Focusing lens |
| 25 | CCD array |
| 26 | Entrance slit |
| 30 | Bulk material |
| $31_t$ | Scanned Area of Bulk material at time t |
| 41 | Reflected energy |
| 42 | Output signals of reflected energy at specific wavelength |
| 43 | Spectral signature |
| 50 | Source of illumination |
| 60 | Control Unit |

The invention claimed is:

1. Real-time bulk material analyzing system for analyzing the elemental characteristics of bulk material passing by on a moving conveyor belt, said system comprising:
   a source of illumination for emitting white light to excite bulk material to be analyzed;
   a spectral sensor for capturing spectral reflectance from bulk material excited by the illumination source; and
   a control unit for comparing the captured spectral reflectance to a stored calibration, wherein:
   said sensor includes a hyperspectral imaging spectrometer producing a two dimensional image, one dimension being a spherical width of the conveyor belt and another dimension being a wavelength of the spectral reflectance, each point of the image representing an amount of energy at a specific wavelength reflected from a specific spot across the conveyor belt, said image data being forwarded to the control unit; and wherein said control unit compares a spectral signature for each specific spot across the conveyor belt having been captured by the spectrometer to a stored calibration, each spectral signature having a continuous spectrum of the amount of energy reflected from the specific spot over a range of wavelengths.

2. Analyzing system as in claim 1, wherein the hyperspectral imaging spectrometer comprises:

a front lens with an entrance slit, said entrance slit being arranged normal to a moving direction of the bulk material passing by the spectrometer to allow reflected energy of only a thin stripe spanning across the bulk material to enter the hyperspectral imaging spectrometer.

3. Analyzing system as in claim 1, wherein the hyperspectral imaging spectrometer comprises:

a prism-grating-prism optics.

4. Analyzing system as in claim 1, wherein the hyperspectral imaging spectrometer produces a one dimensional image, the spherical width of the conveyor belt being reduced to a single value, points of the one dimensional image representing the amount of energy at a specific wavelength reflected across the entire conveyor belt.

5. Analyzing system as in claim 1, wherein the hyperspectral imaging spectrometer comprises:

several spectral sensors, each of said several spectral sensors operating in a frequency region distinct from other sensor frequency regions, said several spectral sensors being arranged as to be co-boresighted.

6. Analyzing system as in claim 1, comprising:

a conveyor belt for conveying bulk material positioned thereon past the illumination source and spectral sensor.

7. Analyzing system as in claim 2, wherein the hyperspectral imaging spectrometer produces a one dimensional image, the spherical width of the conveyor belt being reduced to a single value, points of the one dimensional image representing the amount of energy at a specific wavelength reflected across the entire conveyor belt.

8. Analyzing system as in claim 7, wherein the hyperspectral imaging spectrometer comprises:

several spectral sensors, each of said several spectral sensors operating in a frequency region distinct from other sensor frequency regions, said several spectral sensors being arranged as to be co-boresighted.

9. Analyzing system as in claim 8, comprising:

a conveyor belt for conveying bulk material positioned thereon past the illumination source and spectral sensor.

10. Method for real-time elemental analysis of bulk material being conveyed on a conveyor belt, said method comprising:

illuminating the bulk material with white light to form an illumination spot on the bulk material;

capturing a spectral reflectance from the bulk material excited by the white light with a hyperspectral imaging spectrometer to create a hyperspectral image;

producing said hyperspectral image that comprises a two dimensional image, a first dimension being a width of the illumination spot and a second dimension being a wavelength of the spectral reflectance, each point of the image representing an amount of energy at a specific wavelength reflected from a specific spot in the illumination spot; and comparing said hyperspectral image to a stored calibration representing expected concentrations of previously characterized standards to identify a presence of, and characterize concentrations of, specific elements or their oxides.

11. The method of claim 10, wherein the width of the illumination spot is a spherical width of the conveyor belt.

12. The method of claim 11, wherein the a spectral signature for each specific spot across the conveyor belt having been captured by the spectrometer to a stored calibration, each spectral signature having a continuous spectrum of the amount of energy reflected from the specific spot over a range of wavelengths.

* * * * *